United States Patent [19]

Saito et al.

[11] Patent Number: 4,897,483

[45] Date of Patent: Jan. 30, 1990

[54] AMINO ACID DERIVATIVES AS ANTIHYPERTENSIVES

[75] Inventors: Shizuo Saito; Motoshi Watanabe; Toshiaki Waga; Shinichi Matsui, all of Tokyo, Japan

[73] Assignee: Asahi Breweries Ltd., Tokyo, Japan

[21] Appl. No.: 157,737

[22] Filed: Feb. 18, 1988

[30] Foreign Application Priority Data

Feb. 19, 1987 [JP] Japan .................................. 62-34440
Apr. 7, 1987 [JP] Japan .................................. 62-83885
Jul. 17, 1987 [JP] Japan .................................. 62-180654

[51] Int. Cl.$^4$ .................. C07D 401/12; C07D 209/18; C07D 207/10

[52] U.S. Cl. .................................... 546/201; 546/208; 546/146; 548/452; 548/533

[58] Field of Search ................ 546/201, 208; 548/452, 548/533

[56] References Cited

U.S. PATENT DOCUMENTS 2,208,197 5/1955 Speeter ............................... 546/201

Primary Examiner—Robert T. Bond
Attorney, Agent, or Firm—Felfe & Lynch

[57] ABSTRACT

This invention relates to novel amino acid derivatives which are useful as angiotension converting enzyme inhibitors.

14 Claims, No Drawings

AMINO ACID DERIVATIVES AS ANTIHYPERTENSIVES

BACKGROUND OF THE INVENTION

The present invention relates to novel amino acid derivatives useful as medicines.

U.S. Pat. No. 4,374,829 discloses carboxylalkyl dipeptide derivatives and related compounds which are useful as angiotensin converting enzyme inhibitors and accordingly useful as antihypertensives. U.S. Pat. No. 4,472,384 and U.S. Pat. No. 4,558,037 disclose mixtures of carboxyalkyl dipeptide derivatives with compounds having different pharmacological actions.

SUMMARY OF THE INVENTION

The present invention provides novel amino acid derivatives which are useful as angiotension converting enzyme inhibitors as well as drugs for several kinds of hypertension (ex. hypertension, congestive heart failure, glaucoma).

The compounds of the present invention includes amino acid derivatives represented by the following formula:

$$A-(CH_2)_n CHNHCHCON \cdots \qquad [I]$$

with substituents $COOR_1$, $R_3$, $CH$, $Z$, $COOR_2$, $W$, $B$ wherein

A is amino or a saturated 5 to 6 membered heterocycle having 1 to 2 nitrogen atoms (ex. piperidyl-NH, piperazinyl-N—NH, pyrrolidinyl-N—, morpholinyl-N—O, etc.)

$R_1$ and $R_2$ are each independently hydrogen or lower alkyl;

$R_3$ is lower alkyl or amino lower alkyl (C1–C6); n is 1 to 12, and 7 to 12 only when A is amino;

W and Z are nonexistent, or —CH$_2$— or —CH$_2$CH$_2$—; and

B is nonexistent, or a saturated or unsaturated 5 to 6 membered ring, and pharmaceutically acceptable salts thereof.

The compounds [I] of the present invention are novel compounds, and medical compounds which have strong and lasting angiotensin converting enzyme inhibition activity and are useful as the drugs for several kinds of antihypertensions.

One specific example of the compounds (I) of the present invention is presented by the following formula [I'] and salts thereof.

$$A-(CH_2)_n-CHNHCHCON \begin{array}{c} Ring \\ Q \end{array} X-D \qquad [I']$$

with substituents $COOR_1$, $R_3$, $COOR_2$ wherein

A is $NH_2$ or piperidyl-NH;

n is 1 to 12, and 7 to 12 only when A is —NH$_2$;

$R_1$ and $R_2$ are each independently hydrogen or lower alkyl;

$R_3$ is —CH$_3$ or —CH$_2$CH$_2$CH$_2$CH$_2$NH$_2$;

X is —CH$_2$— or —CH$_2$CH$_2$—;

D is nonexistent, or benzene or cyclohexane ring which forms a condensed ring together with ring Q.

One group of compounds of the present invention represented by the general formula [I] include alanine derivatives represented by the following formula [Ia] and salts thereof.

$$A-(CH_2)_n CHNHCHCON-Y \qquad [Ia]$$

with substituents $COOR_1'$, $CH_3$ wherein

A is amino or piperidyl-NH;

Y is pyrrolidinyl-COOR$_2$, tetrahydroisoquinolinyl-COOR$_2$, or octahydroisoquinolinyl-COOR$_2$;

$R_1$ and $R_2$ are each independently hydrogen or alkyl having 1 to 4 carbon atoms, and n is 1 to 10, and 7 to 10 only when A is amino.

As the typical compounds belonging to said group, there can be enumerated

N-[1(S)-carboxy-8-aminooctyl]-L-alanyl-L-proline,
N-[1(S)-ethoxycarbonyl-8-aminooctyl]-L-alanyl-L-proline,
N-[1(S)-carboxy-9-aminononyl]-L-alanyl-L-proline, N-[1(S)-ethoxycarbonyl-9-aminononyl]-L-alanyl-L-proline,
N-[1(S)-carboxy-10-aminodecyl]-L-alanyl-L-proline,
N-[1(S)-ethoxycarbonyl-10-aminodecyl]-L-alanyl-L-proline,
N-[1(S)-carboxy-3-(4-piperidyl)propyl]-L-alanyl-L-proline,
N-[1(S)-ethoxycarbonyl-3-(4-piperidyl)propyl]-1-alanyl-L-proline,
N-[1(S)-carboxy-5-(4-piperidyl)pentyl]-L-alanyl-L-proline,
N-[1(S)-ethoxycarbonyl-5-(4-piperidyl)pentyl]-L-alanyl-L-proline,
N-[1(S)-carboxy-6-(4-piperidyl)hexyl]-L-alanyl-L-proline,
N-[1(S)-ethoxycarbonyl-6-(4-piperidyl)hexyl]-L-alanyl-L-proline,
1-[N-[1(S)-carboxy-6-(4-piperidyl)hexyl]-L-alanyl]-(2α,3aβ,7aβ)-octahydro-1H-indole-2(S)-carboxylic acid,
1-[N-[1(S)-carboxy-5-(4-piperidyl)penthyl]-L-alanyl]-(2₆₀,3aβ,7aβ)-octahydro-1H-indole-2(S)-carboxylic acid,
1-[N-[1(S)-carboxy-8-aminooctyl]-L-alanyl]-1,2,3,4-tetrahydroisoquinoline-3(S)-carboxylic acid,
2-[N-[1(S)-ethoxycarbonyl-8-aminooctyl]-L-alanyl]-1,2,3,4-tetrahydroisoquinoline-3(S)-carboxylic acid,
2-[N-[1(S)-carboxy-5-(4-piperidyl)pentyl]-L-alanyl]-1,2,3,4-tetrahydroisoquinoline-3(S)-carboxylic acid,
2-[N-[1(S)-ethoxycarbonyl-5-(4-piperidyl)pentyl]-L-alanyl]-1,2,3,4-tetrahydroisoquinoline-3(S)-carboxylic acid,
2-[N-[1(S)-carboxy-6-(4-piperidyl)hexyl]-L-alanyl]-1,2,3,4-tetrahydro isoquinoline-3(S)-carboxylic acid,
2-[N-[1(S)-ethoxycarbonyl-6-(4-piperidyl)hexyl]-L-alanyl]-1,2,3,4-tetrahydro isoquinoline-3(S)-carboxylic acid,
1-[N-[1(S)-ethoxycarbonyl-6-(4-piperidyl)hexyl]-L-alanyl]-(2α,3aβ,7aβ)-octahydro-1H-indole-2(S)-carboxylic acid,
1-[N-[1(S)-ethoxycarbonyl-5-(4-piperidyl)pentyl]-L-alanyl]-(2α,3aβ,7aβ)-octahydro-1H-indole-2(S)-carboxylic acid, and the like
and pharmaceutically acceptable salts thereof.

The second group of the compounds of the present invention represented by the general formula [I] includes lysine derivatives represented by the following formula [Ib] and salts thereof:

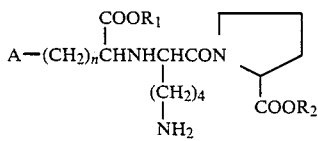

[Ib]

wherein
A is amino or /

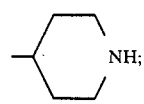

$R_1$ and $R_2$ are each independently hydrogen or alkyl having 1 to 4 carbon atoms; n is 3 to 8, and 7 to 8 when A is amino.

As the preferable compounds belonging to the second group, there can be enumerated
$N^\alpha$-[1(S)-carboxy-8-aminooctyl]-L-lysyl-L-proline,
$N^\alpha$-[1(S)-ethoxycarbonyl-8-aminooctyl]-L-lysyl-L-proline,
$N^\alpha$-[1(S)-carboxy-5-(4-piperidyl)pentyl]-L-lysyl-L-proline,
$N^\alpha$-[1(S)-carboxy-6-(4-piperidyl)hexyl]-L-lysyl-L-proline, and the like,
and pharmaceutically acceptable salts thereof.

The compounds [I] of the present invention have three asymmetric carbon atoms and contain eight kinds of optical isomers. The present invention includes every one of those compounds. As preferable compounds of these isomers, there may be enumerated those in which every one of said three asymmetric carbon atoms is of S configuration.

The compounds [I] of the present invention, which are used as medicines, may take the free form, and further take the form of pharmaceutically acceptable salts. As the pharmaceutically acceptable salts of the compounds, there may be enumerated inorganic salts with alkali metal such as sodium, potassium and lithium, alkali earth metal such as calcium and magnesium, and inorganic acid salts such as hydrochloride, hydrobromide salt, sulfate salt and phosphate salt; or organic salts of organic bases such as lysine salt, ornithine salt, dicyclohexylamine salt and organic acid salts such as succinic acid salt, maleate, fumaric acid salt and methanesulfonic acid salt.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

According to the present invention, the compounds [I] can be produced by reacting the compounds represented by the following general formula:

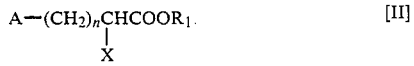

[wherein, X is chlorine, bromine, iodine and alkylsulfonyloxy. A is the same as defined above and may include properly protected amino and imino, n and $R_1$ are each the same as defined above.]
with the compounds represented by the following formula:

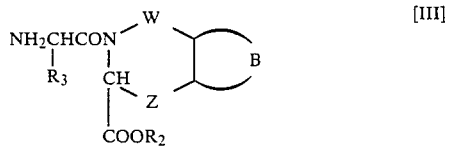

[III]

[wherein, $R_2$, $R_3$, W, Z and B are each the same as defined above. $R_2$ may include benzyl, and
$R_3$ may include properly protected aminoalkyl.] to thereby obtain protected condensates, and then removing protective bases by pertinent means.

Furthermore, the compounds [I] can be produced by reacting ketone represented by the following general formula:

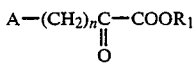

[wherein, n, $R_1$ and A are each the same as defined above, and A may include properly protected amino and imino.]

with the compounds [III] in the presence of reducing agents to thereby obtain protected condensates, and then removing protective bases by pertinent means.

Still further, the compounds [I] of the present invention can be produced by coupling carboxylic acid represented by the following general formula:

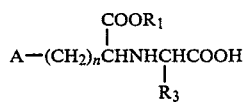

[wherein, n, $R_1$, $R_3$ and A are each the same as defined above. A may include properly protected amino and imino. $R_3$ may include properly protected aminoalkyl.]

with the compounds represented by the following formula:

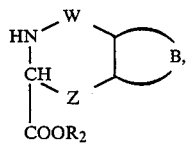

[wherein, $R_2$, W, Z and B are each the same as defined above. $R_2$ may include benzyl.]

to thereby obtain protected condensates, and then removing protective bases by pertinent means.

The above-mentioned reaction shall be explained in detail hereinafter.

The reaction between the compound [II] and the compound [III] may be practiced in a desired solvent and in the presence of deacidifiable agent. As said deacidifiable agents, there may be suitably used alkali carbonate such as potassium carbonate, sodium carbonate, sodium bicarbonate and the like; and organic tertiary amines such as triethylamine, N-methylmorpholine and the like. As said solvents, there may be used dimethylformamide, acetonitrile, chloroform and the like. The reaction temperature is suitably in the range of about −20° C. to 120° C., and may be selected appropriately according to the properties of materials-compounds to be produced.

The compound [III] and the compound [IV] may be condensed under reducing conditions.

As said reducing conditions, there may be enumerated the reaction conditions for the catalytic reduction using metals such as platinum palladium, Raney nickel, rhodium and the like and mixtures of said metals with optional carriers as catalysts; the reduction using metallic hydro-compounds such as lithiumaluminiumhydride, lithiumborohydride, lithiumcyanoborohydride, sodiumborohydride, sodiumcyanoborohydride and the like; the reduction using metallic sodium and metallic magnesium with alcohols; the reduction using metals such as iron, zinc and the like with acids such as hydrochloric acid, acetic acid and the like; the electrolytic reduction and the reduction using reductase. The above-mentioned reaction is normally carried out in water or organic solvents (for instance, methanol, ethanol, ethyl ether, dioxane, methylene chloride, chloroform, benzene, toluene, dimethylformamide, dimethylacetamide and the like. The reaction temperature, which is different depending on reducing means, is normally preferred to be in the range of about −20° C.−+100° C.

This reaction can fully attain the object under atmospheric pressure, but may be carried out under pressurization or reduced pressure as occasion demands. In the condensation reaction between the compound [V] and the compound [VI], as the reactive derivatives in the carboxyl group of the compound [V] there can be enumerated derivatives of acid halides such as acid chloride, acid bromide and the like; acid anhydrides obtained by dehydrating one water molecule from two molecules of [V]; mixed anhydrides obtained by substituting the hydrogen of the carboxyl group of [V] by for instance ethoxycarbonyl group, isobutyloxycarbonyl group, isobutyloxycarbonyl group, benzyloxycarbonyl group and the like. The reaction is generally practiced in a suitable solvent. As said solvent there may be used any solvent which does not inhibit the reaction. When [V] is used without converting [V] into the reactive derivatives, it is profitable to practice the reaction in the presence of dehydrating reagents such, for instance, as dicyclohexycarbodiimide, carbonyldiimidazole, diethyl cyanophosphate, diphenylphosphoryl azide and the like. It is also possible to practice the reaction in the presence of bases such as pyridine, picoline, triethylamine, sodium hydroxide and the like. The reaction temperature is usually in the range of about −20° to +150° C. In the almost cases the reaction well proceeds even under atmospheric temperature.

The thus obtained condensates can be isolated and purified from the reaction mixtures by means of usual separating and purifying means such, for instance, as extraction, concentration, neutralization, filtration, recrystallization, column chromatography, thin layer chromatography and the like. If needed, the condensates is subjected to deprotecting reaction by the means well known in peptide chemistry including acid treatment using hydrochloric acid, trifluoroacetic acid and the like; alkali saponification using aqueous solutions of sodium hydroxide, potassium hydroxide, lithium hydroxide and the like; and catalytic reduction using metal catalysts of palladium black, palladium/carbon, platinum oxide and the like, and thereby anticipated products [I] or salts thereof are obtained.

In the compound represented by the formula [I], which has three asymmetric carbon atoms in the molecule, there exist eight optical isomers. As mentioned above, both these isomers and their mixtures are included within the range of the present invention. Accordingly, these isomers may also be prepared separately by request.

That is, when at least one of the material compounds is racemic, [I] is normally obtained in the form of an isomeric mixture, but this isomeric mixture may be separated into each isomer by using a known separating method such, for instance, as fractional recrystallization, various chromatographies and the method for producing salts of optically active bases or acids. When the above-mentioned reaction is practiced by using one of each of the previously optically definite material compound, there can be obtained an optical isomer of [I].

The compounds represented by the formula [I] are angiotensin converting engyme inhibitors and bradykinin cracking enzyme inhibitors and have prolonged and strong antihypertensive actions, so that those compounds are useful as not only antihypertensive but for medical treatment of glaucoma or congestive heart failure.

The evaluation of converting enzyme inhibitors is introduced from the analysis of enzyme inhibition in a test tube. One example of inhibition activity of the compounds of the present invention calculated from the method of Friedland & Silverstein [Am. J. Clin. Pathol. 66, 416 (1976)] is as shown in the following table.

TABLE $$A-(CH_2)_n\underset{R_3}{\underset{|}{CH}}NH\underset{\underset{COOR_2}{\overset{|}{CH}}}{\underset{|}{CH}}CON\overset{W}{\underset{Z}{\diagdown}}B \qquad \overset{COOR_1}{\overset{|}{}}$$

| Compound No. | Example No. | A | n | $R_1$ | $R_3$ | $\begin{array}{c}N\diagdown W\\|\\CH\diagdown Z\\|\\COOR_2\end{array}$ B | $IC_{50}(M)^*$ | AUC** (iv) |
|---|---|---|---|---|---|---|---|---|
| 1 | I | NH$_2$ | 7 | H | CH$_3$ | N-pyrrolidine-COOH | $7.5 \times 10^{-10}$ | 509 |
| 2 | V | HN-piperidine | 4 | " | " | " | $1.0 \times 10^{-9}$ | 429 |
| 3 | VI | " | 5 | " | " | " | $1.1 \times 10^{-9}$ | 424 |
| 4 | VII | NH$_2$ | 7 | " | —(CH$_2$)$_4$NH$_2$ | " | $7.0 \times 10^{-10}$ | 431 |
| 5 | VIII | HN-piperidine | 4 | " | " | " | $1.0 \times 10^{-9}$ | 460 |
| 9 | XII | " | 5 | " | —(CH$_2$)$_4$NH$_2$ | N-pyrrolidine-COOH | $1.0 \times 10^{-9}$ | — |
| 10 | XIII | " | 5 | " | CH$_3$ | N-bicyclic-COOH | $9.0 \times 10^{-10}$ | — |
| 11 | XIV | " | 4 | " | " | " | $6.2 \times 10^{-10}$ | — |
| 12*** | — | NH$_2$ | 6 | " | " | N-pyrrolidine-COOH | $1.4 \times 10^{-9}$ | 368 |

*Concentration inhibiting 50% of the activity of rabbit lung ACE was determined by the method of Friedland and Silverstein.
**Angiotensin I (AI, 300 ng/Kg) were injected into the femoral vein at intervals of 10 min until the constant pressor response to AI was obtained. The AI challenges were repeated 10, 20, 30, 40, 50, 60, 90, 120, 180, 300 and 360 min after i.v. administration of the test compound (50 μg/Kg), and AVC (area under the curve) was calculated by the AI inhibition response vs. time curves for 0 to 360 min.
***One of the compounds disclosed in U.S. Pat. No. 4374829

The angiotensin converting enzyme inhibitors of the present invention may be used for mammals such as monkey, dog, cat, rat, human and the like. The compound of the present invention favorably may be blended in pharmaceutical preparations in the conventional manner. These compounds are made to take the common dosage form such as capsule, tablet, sugar-coating tablets, granule, solution, syrup, ointment, emulsion and the like and/or the depo form. The active substances may also exist in the microcapsulated form according to circumstances. The compound of the present invention may contain acceptable organic or inorganic auxiliary ingredients such, for instance, as granule-forming agents, adhesive and binder, lubricants, suspending agents, resolvent antibiotics, humectant and preservatives.

In the case where our compound is applied by parenteral, peroral and topical applications, about 0.5 to 50 mg is dosed 1 to 3 times per day. The topically used preparation may contain our compounds in an amount of 0.001 to 5 wt.%, and its dosage may be changed depending upon the condition of sickness, the weight of a patient and other factors recognized by a doctor.

The compound of the present invention may be used together with other diuretics or antihypertensives. As diuretics there may be enumerated those such, for instance, as hydrochlorothiazide, furosemide and the like. As antihypertensives, there is used beta-blocker such as propranolol, thymolol, methyldopa and the like.

Auxiliary ingredients which may be mixed with tablets, capsules or minute glanules and the like are shown as follows, namely binder such as traganth, gum arabic, corn starch and gelatin: excipient such as micro-crystal cellulose: swelling agents such as corn starch, pregelatinized starch, alginic acid and the like: lubricants such as magnesium stearate and the like: sweetening agents such as sucrose, lactose, sacharin and the like: and flavor such as peppermint, oil of wintergreen and cherry. When the unit preparation form of medicines is capsule, the above-mentioned type of materials may further contain liquid carriers such as fatty oil and the like. Various other material may be present as coatings or to otherwise modify the phydical form of the dosage unit. For instance, tablets may be coated with shellac, sugar or both. A sirup or elixir may contain active compounds; sweeting agents such as sucrose and the like; preservatives such as methyl and propylparaben; coloring matters; and a flavoring agent such as cherry and orange.

The sterile composite for injection may be prescribed according to conventional medical preparation by dissolving or suspending the active substance in the vehicle such as injectable water, a naturally occurring vegetable oil such as sesame oil, coconut oil, peanut oil, cottonseed oil and the like or in the synthetic fatty vehicle such as ethyl oleate or the like. Buffering agents, preservatives, antioxidants and the like can be added to the sterile composite as required.

Referring to the suppository, cacao butter and witepsol are used as bases, and carbowax is used as hydrophilic base. Said suppository may contain surface active agents, coloring agents, antioxidants.

The sterile composite used locally in eyes is prescribed in combination with the pharmaceutically acceptable carrier substance such, for instance, as aqueous methylcellulose. This combination may be practiced in the form of suspension, solution, ointment, emulsion or opthalmological insertion. This sterile composite may be prepared in the combination with such a compound as benzalkonium chloride having a preservative action.

EXAMPLE I

N-[1(S)-carboxy-8-aminooctyl]-L-alanyl-L-proline (a)
N-[1(S)-ethoxycarbonyl-8-phthalimidooctyl]-L-alanyl-L-proline tertiary butylester A solution of ethyl 2-bromo-9-phthalimidononanoate [prepared according to Chem. Pharm. Bull. 34, 2078 (1986)] (3 g), L-alanyl-L-proline tertiary butylester (1 g) and triethylamine (0.8 ml) in acetonitrile (200 ml) is subjected to 60 hours' reflux. Acetonitrile is distilled off under reduced pressure, and the residue is dissolved in ethyl acetate. The solution is dehydrated with anhydrous sodium sulfate, and thereafter is concentrated to obtain an oily residue. When this substance is applied to a silica gel chromatography (ethyl acetate:n-hexane=3:1) for separative purification, 310 mg of N-[1(R)-ethoxycarbonyl-8-phthalimidooctyl]-L-alanyl-L-proline tertiary butylester is obtained as a colorless oil from the first effluence.

Thin layer chromatography (TLC), Rf=0.33 (Developing Solvent:A, Ethyl acetate:n-hexane=3:1; Detection:peptide reagent).

NMR(CDCl$_3$) δ:
1.1–2.4(32H, m), 3.05–3.3(1H, m),
3.4–3.75(4H, m), 3.9–4.5(4H, m),
7.5–7.85(4H, m).

N-[1(S)-ethoxycarbonyl-8-phthalimidooctyl]-L-alanyl-L-proline tertiary butylester (300 mg) is further obtained as a colorless oil from the following effluence.

TLC, Rf=0.25 (Developing Solvent:A, Detection:-peptide reagent)

NMR(CDCl$_3$) δ:
1.1–2.2(32H, m), 3.0–3.3(1H, m),
3.35–3.75(4H, m), 3.9–4.5(4H, m),
7.5–7.9(4H, m)

(b) N-[1(S)-ethoxycarbonyl-8-tertiary butoxycarbonylaminooctyl]-L-alanyl-L-proline tertiary butylester N-[1(S)-ethoxycarbonyl-8-phthalimidooctyl]-L-alanyl-L-proline tertiary butylester (300 mg) is dissolved in 8 ml of anhydrous ethanol. Then, 1 ml of ethanol solution containg hydrazinehydrate (180 mg) is dropped in the solution, and this solution is allowed to stand overnight at room temperature. The reaction mixture is added to ethyl acetate (50 ml), and washed with 0.1N aqueous sodium hydroxide and water. Then, the ethyl acetate solution is added with 5 ml of 3% aqueous sodium bicarbonate and 75 mg of (Boc)$_2$O, and the whole is stirred for 3 hours. The ethyl acetate layer is separated, dried with anhydrous sodium sulfate, and the solvent is distilled off under reduced pressure. When the residue is applied to a column chromatography (silica gel 30 g), which is eluted with the solvent (ethyl acetate:n-hexane=3:1). An effluence is collected and concentrated to yield a colorless oil (130 mg).

TLC, Rf=0.25 (Developing Solvent:A, Detection:-peptide reagent).

NMR(CDCl$_3$) δ:
1.1–1.8(36H, m), 1.8–2.0(5H, m),
2.8–3.7(5H, m), 3.9–4.7(5H, m).

(c)
N-[1(S)-ethoxycarbonyl-8-aminooctyl]-L-alanyl-L-proline

The compound (130 mg) obtained according to Example I b) is dissolved in 99% formic acid (100 ml), and the solution is stirred at 37° C. for 48 hours. Formic acid is distilled under reduced pressure, and the residue is washed with ether and thereafter dryed under reduced pressure to give a colorless oil (90 mg).
TLC, Rf=0.23 (Developing Solvent:B,
n-butanol:acetic acid:
water=4:1:2; Detection:ninhydrine)

(d) N-[1(S)-carboxy-8-aminooctyl]-L-alanyl-L-proline

To the oil obtained according to Example I c), 3 ml of 1N aqueous sodium hydroxide is added, and the solution is stirred for 2 hours. Then, the reaction mixture is dropped in cation ion-exchange resin DOWEX 50W-X2 (20 ml), and stirred for 30 minutes. The fractions eluted with 2% aqueous pyridine are collected and subjected to freeze drying to obtain 75 mg of colorless white powder.
TLC, Rf=0.17 (Developing Solvent:B, Detection:-ninhydrine).
NMR(CD$_3$OD) δ:
1.2–2.4(19H, m), 2.7–3.1(2H, m),
3.3–3.8(3H, m), 3.9–4.7(2H, m).

EXAMPLE II
N-[1(S)-carboxy-9-aminononyl]-L-alanyl-L-proline (a)
N-[1(S)-ethoxycarbonyl-9-phthalimidononyl]-L-alanyl-L-proline tertiary butylester Ethyl 2-bromo-10-phthalimidodecanoate (12 g) [prepared according to Chem. Pharm. Bull, 34, 2078 (1986)] is used as starting material, and is subjected to reaction and purification in the same manner as Example I a), thereby obtaining 1.4 g of oil.
TLC, Rf=0.31 (Developing Solvent:A, Detection:-peptide reagent)
NMR (CDCl$_3$) δ:
1.1–2.25(34H, m), 3.0–3.3(1H, m),
3.35–3.8(4H, m), 3.85–4.5(4H, m),
7.5–7.85(4H, m).

(b) N-[1(S)-ethoxycarbonyl-9-tertiary butoxycarbonylaminononyl]-L-alanyl-L-proline tertiary butylester The compound obtained by Example II a) (1.3 g) is reacted and purified according to the procedure as shown in Example I b) to obtain 690 mg of oil.
TLC, Rf=0.31 (Developing Solvent:A, Detection:-peptide reagent).
NMR(CDCl$_3$) δ:
1.1–1.7(38H, m), 1.8–2.3(5H, m),
2.8–3.7(5H, m), 3.8–4.9(5H, m).

(c)
N-[1(S)-ethoxycarbonyl-9-aminononyl]-L-alanyl-L-proline

The compound obtained by Example II b) (600 mg) is subjected to deprotecting reaction according to the procedure as shown in Example I c) to obtain 440 mg of oil.
TLC, Rf=0.29 (Developing Solvent:A, Detection:-ninhydrine).

(d) N-[1(S)-carboxy-9-aminononyl)-L-alanyl-L-proline

The compound obtained by Example II c) (420 mg) is subjected to alkali hydrolysis according to the procedure as shown in Example I d) and the reaction mixture treated with cation ion-exchange resin to obtain 200 mg of white powder.
TLC, Rf=0.23 (Developing Solvent:B, Detection:-ninhydrine).
NMR(CD$_3$OD) δ:
1.1–2.3(21H, m), 2.6–3.0(2H, m),
3.3–3.7(3H, m), 3.8–4.5(2H, m).

EXAMPLE III
N-[1(S)-carboxy-10-aminodecyl]-L-alanyl-L-proline (a)
N-[1(S)-ethoxycarbonyl-10-phthaimidodecyl]-L-alanyl-L-proline tertiary butylester Ethyl 2-bromo-11-phthalimidoundecanoate (2.4 g) [prepared according to Chem. Pharm. Bull. 34, 2078 (1986)] is used as starting material, and reacted and purified according to the same procedure as shown in Example I(a), thereby obtaining 1.4 g of oily substance.
TLC, Rf=0.36 (Developing Solvent:A, Detection:-peptide reagent).
NMR(CDCl$_3$) δ:
1.0–2.2(36H, m), 3.0–3.3(1H, m),
3.3–3.75(4H, m), 3.9–4.5(4H, m), 7.5–7.8(4H, m).

(b) N-[1(S)-ethoxycarbonyl-10-tertiary butoxycarbonylaminodecyl]-L-alanyl-L-proline tertiary butylester The compound obtained by Example III a) (900 mg) is reacted and purified according to the procedure as shown in Example I b), to obtain 570 mg of oil.
TLC, Rf=0.36 (Developing Solvent:A, Detection:-peptide reagent).
NMR(CDCl$_3$) δ:
1.1–1.8(40H, m), 1.9–2.2(5H, m),
2.8–3.7(5H, m), 3.8–4.7(5H, m).

(c)
N-[1(S)-ethoxycarbonyl-10-aminodecyl]-L-alanyl-L-proline

The compound obtained by Example III b) (500 mg) is subjected to deprotecting reaction according to the procedure as shown in Example I c), to obtain 470 mg of oil.
TLC, Rf=0.33 (Developing Solvent:B, Detection:-ninhydrine).

(d) N-[1(S)-carboxy-10-aminodecyl]-L-alanyl-L-proline

The compound obtained by Example III c) (400 mg) is subjeced to alkali hydrolysis according to the procedure as shown in Example I d), and the reaction mixture is treated with cation ion-exchange resin to obtain 210 mg of white powder.
TLC, Rf=0.28 (Developing Solvent:B, Detection:-ninhydrine).
NMR(CD$_3$OD) δ:
1.1–2.5(23H, m), 2.6–3.1(2H, m),
3.1–3.8(3H, m), 3.8–4.5(2H, m).

EXAMPLE IV

N-[1(S)-carboxy-3-(4-piperidyl)propyl]-L-alanyl-L-proline (a)

N-[1(S)-ethoxycarbonyl-3-(1-benzyloxycarbonyl-4-piperidyl)propyl]-L-alanine tertiary butylester Ethyl 4-(1-benzyloxycarbonyl-4-piperidyl)-2-oxo butanoate [prepared according to Chem. Pharm. Bull, 34, 3747 (1986)] (3.1 g), L-alanine tertiary butylester.hydrochloride (0.65 g), molecular sieves 3A (60 g) and triethylamine (0.36 g) are added to ethanol (100 ml). A solution of sodiumcyanoborohydride (0.45 g) in ethanol (10 ml) is dropped in the said mixture. The reaction mixture is stirred overnight at room temperature. Thereafter, the molecular sieves 3A is filtered off and the ethanol is distilled out under reduced pressure. The residue is then applied to a silica gel chromatography (n-hexane:ethyl acetate=2:1) to obtain, from the first effluence, 280 mg of N-[1(R)-ethoxycarbonyl-3-(1-benzyloxycarbonyl-4-piperidyl)propyl]-L-alanine tertiary butylester as colorless oil.

TLC, Rf=0.40 (Developing Solvent:C, n-hexane:ethyl acetate=2:1, Detection:peptide reagent).

From the following effluence, 670 mg of N-[1(S)-ethoxycarbonyl-3-(1-benzyloxycarbonyl-4-piperidyl)-propyl]-L-alanine tertiary butylester (including unidentified compounds) is further obtained.

TLC, Rf=0.29 (Developing Solvent:C, Detection:-peptide reagent).

(b)

N-[1(S)-ethoxycarbonyl-3-(1-benzyloxycarbonyl-4-piperidyl)propyl]-L-alanyl-L-proline benzylester N-[1(S)-ethoxycarbonyl-3-(1-benzyloxycarbonyl-4-piperidyl)propyl]-L-alanine tertiary butylester (including unidentified compounds) is added with formic acid. This mixture is left standing at 40° C. for 40 hours. Thereafter, the reaction mixture is treated with cation ion-exchange resin DOWEX 50W-X2 and the fractions eluted by 2% pyridine is freeze-dried. Then, the product (80 mg) and proline benzylester.hydrochloride (53 mg) are dissolved in dimethylformamide (5 ml). Triethylamine (70 μl) and diethyl cyanophosphate (46 mg) are dropped with stirring in the solution under cooling with ice. After standing at room temperature for 30 minutes, the reaction mixture is added with water (100 ml), and extracted therefrom with ethyl acetate.

The ethyl acetate layer is further washed with aqueous 10% phosphoric acid (50 ml×2), aqueous 1N sodium hydroxide (50 ml) and water (100 ml×2), and finally dried with anhydrous sodium sulfate.

Ethyl acetate is distilled out under reduced pressure, and the resulting residue is purified by silica gel chromatography (hexane:ethyl acetate=1:10) to obtain a colorless oil (92 mg).

TLC, Rf=0.28 (Developing Solvent:D, hexane:ethyl acetate=1:10, Detection:peptide reagent).

NMR(CDCl$_3$) δ:
1.0–2.3(18H, m), 2.4–3.7(7H, m),
3.8–4.7(6H, m), 5.1(4H, s), 7.3(10H, s).

(c)

N-[1(S)-ethoxycarbonyl-3-(4-piperidyl)propyl]-L-alanyl-L-proline

The oily substance obtained by Example IV b) (92 mg) is dissolved in 30 ml of methanol. Palladium black (100 mg) is added to this solution for catalytic reduction. After completion, the palladium black is filtered off, and the methanol is distilled off from the filtrate under reduced pressure, to obtain 62 mg of colorless oily substance.

TLC, Rf=0.11 (Developing Solvent:B, Detection:-peptide reagent).

(d)

N-[1(S)-carboxy-3-(4-piperidyl)propyl]-L-alanyl-L-proline

The oily substance obtained by Example IV c) (62 mg) is added with 1.5 ml of aqueous 1N sodium hydride, and this is left standing at room temperature for 1 hour.

Then, the reaction mixture is treated with cation ion-exchange resin DOWEX 50W-X2. The fractions eluted with aqueous 2% pyridine were subjected to freeze drying to obtain 46 mg of white powder.

TLC, Rf=0.09 (Developing Solvent: B, Detection: peptide reagent).

NMR (D$_2$O) δ:
1.0–2.4(16H, m), 2.6–3.3(6H, m),
3.4–4.5 (3H, m).

EXAMPLE V

N-[1(S)-carboxy-5-(4-piperidyl)pentyl]-L-alanyl-L-proline (a)

N-[1(S)-ethoxycarbonyl-5-(1-benzyloxycarbonyl-4-piperidyl)pentyl]-L-alanine tertiary butylester Ethyl 6-(1-benzyloxycarbonyl-4-piperidyl)-2-chlorohexanoate (prepared according to Chem. Pharm. Bull. 34, 3747 (1986)] (5.5 g), L-alanine tertiary butylester.hydrochloride (1.4 g), triethylamine (1.9 g), KI (5.0 g) and CH$_3$CN (250 ml) is heated under reflux for 3 days. The mixture is evaporated in vacuo and the residue is purified according to the same procedure as shown in Example IV a), to give 1.5 g of oil.

TLC, Rf=0.55 (Developing Solvent: C, Detection: peptide reagent).

(b)

N-[1(S)-ethoxycarbonyl-5-(1-benzyloxycarbonyl-4-piperidyl)pentyl]-L-alanyl-L-proline benzylester The compound obtained by Example V a) was reacted and purified according to the same procedure as shown in Example IV b), to obtain 240 mg of oily matter.

TLC, Rf=0.38 (Developing Solvent: D, Detection: peptide reagent).

NMR (CDCl$_3$) δ:
1.0–2.4(22H, m), 2.5–3.8(7H, m),
3.9–4.7(6H, m), 5.1(4H, s), 7.3(10H, s).

(c)

N-[1(S)-ethoxycarbonyl-5-(4-piperidyl)pentyl]-L-alanyl-L-proline

The oily matter obtained by Example V b) (220 mg) is used. This oily substance is reacted and purified according to the procedure as shown in Example IV c) to obtain 140 mg. of oil.

TLC, Rf=0.19 (Developing Solvent: B, Detection: peptide reagent).

(d)
N-[1(S)-carboxy-5-(4-piperidyl)pentyl]-L-analyl-L-proline

The oily substance obtained by Example V c) (90 mg) was used. This oil is reacted and purified according to the procedure as shown in Example IV d) to obtain 60 mg of white powder.
TLC, Rf=0.11 (Developing Solvent: B, Detection: peptide reagent).
NMR (D$_2$O) δ:
1.0–2.4(20H, m), 2.6–3.3(6H, m),
3.4–4.5(3H, m).

EXAMPLE VI

N-[1(S)-carboxy-6-(4-piperidyl)hexyl]-L-alanyl-L-proline (a)
N-[1(S)-ethoxycarbonyl-6-(1-benzyloxycarbonyl-4-piperidyl)hexyl]-L-alanine tertiary butylester Ethyl 7-(1-benzyloxycarbonyl-4-piperidyl)-2-oxoheptanoate [prepared according to Chem. Pharm. Bull. 34, 3747 (1986)] (4.35 g) is used as starting material, and reacted and purified according to the same procedure as shown in Example IV a), to obtaun 425 ml of oily substance.
TLC, Rf=0.50 (Developing Solvent: C, Detection: peptide reagent).

(b)
N-[1(S)-ethoxycarbonyl-6-(1-benzyloxycarbonyl-4-piperidyl)hexyl]-L-alanyl-L-proline benzylester The compound obtained by Example VI a) (425 mg) is used as starting material, and reacted and purified according to the procedure as shown in Example IV b) to obtain oil (430 mg).
TLC, Rf=0.50 (Developing Solvent: A, Detection: peptide reagent).
NMR (CDCl$_3$) δ:
1.0–2.4(24H, m), 2.5–3.8(7H, m),
3.9–4.7(6H, m), 5.1(4H, s). 7.3(10H, s).

(c)
N-[1(S)-ethoxycarbonyl-6-(4-piperidyl)hexyl]-L-alanyl-proline

The oil (430 mg) obtained by Example VI b) is used as starting material, and reacted and purified according to the same procedure as Example IV c), to obtain 290 mg of oil.
TLC, Rf=0.30 (Developing Solvent: B, Detection: peptide reagent).

(d)
N-[1(S)-carboxy-6-(4-piperidyl)hexyl]-L-alanyl-L-proline

The oil (290 mg) obtained by Example VI c) is used as starting material, and reacted and purified according to the procedure as Example IV d), to obtain 220 mg of light-yellow powder.
TLC, Rf=0.19 (Developing Solvent: B, Detection: peptide reagent)
NMR (D$_2$O) δ:
1.0–2.4(22H, m), 2.6–3.3(6H, m),
3.4–4.5(3H, m).

EXAMPLE VII

N$^\alpha$-[1(S)-carboxy-8-aminooctyl]-L-lysyl-L-proline (a)
N$^\alpha$-(1-ethoxycarbonyl-8-phthalimidooctyl)-N$^\epsilon$-tertiary butoxycarbonyl-L-lysyl-L-proline tertiary butylester A solution of ethyl 2-bromo-9-phthalimidononanoate [prepared according to Chem. Pharm. Bull. 34, 2078 (1986)] (2.5 g), N$^\epsilon$-tertiary butoxycarbonyl-L-lysyl-L-proline tertiary butylester (1 g) and triethylamine (0.8 ml) in acetonitrile (150 ml) is refluxed for 48 hours. The acetonitrile is distilled under reduced pressure, and the residue is dissolved in ethyl acetate. The solution is dried with anhydrous sodium sulfate, and thereafter is concentrated to obtain an oil. This oil is applied to silica gel chromatography (ethyl acetate:n:hexane=1:1) to obtain a diastereomer mixture.
TLC, Rf=0.22 (Developing Solvent E,ethyl acetate:n-hexane=1:1).

(b) N$^\alpha$-[1(S)-ethoxycarbonyl-8-tertiary butoxycarbonylaminooctyl]-N$^\epsilon$-tertiary butoxy carbonyl-L-lysyl-L-proline tertiary butylester N$^\alpha$-(1-ethoxycarbonyl-8-phthalimidooctyl)-N$^\epsilon$-tertiary butoxycarbonyl-L-lysyl-L-proline tertiary butylester (1 g) is dissolved in 300 ml of anhydrous ethanol. Then, 3 ml of ethanol solution of hydrazine hydrate (550 mg) is dropped in the solution, and the reaction mixture is left standing overnight at room temperature. The reaction mixture is then added to ethyl acetate (300 ml). The ethyl acetate solution is washed with water and aqueous 0.1N sodium hydroxide and concentrated under reduced pressure to 100 ml. To this concentrated solution, 60 ml of aqueous 3% sodium bicarbonate and 800 mg of (Boc)$_2$O is added. The reaction mixture is stirred for 3 hours. The ethyl acetate layer is washed with water, and dried with anhydrous sodium sulfate. The solvent is distilled under reduced pressure. The residue is applied to a column chromatography (silica gel 150 g) (Developing Solvent, ethyl acetate:n-hexane=2:1) to obtain 500 mg of N$^\alpha$-[1(R)-ethoxycarbonyl-8-tertiary butoxycarbonylaminooctyl]-N$^\epsilon$-tertiary butoxycarbonyl-L-lysyl-L-proline tertiary butylester (Rf=0.65, Developing Solvent F, ethyl acetate:n-hexane=2:1) from the first effluent, and 510 mg of N$^\alpha$-[1(S)-ethoxycarbonyl-8-tertiary butoxycarbonylaminooctyl]-N$^\epsilon$-tertiary butoxycarbonyl-L-lysine-L-proline tertiary butylester (Rf=0.56, Developing Solvent F, ethyl acetate:n-hexane=2:1) from the following effluence.

(c)
N$^\alpha$-[1(S)-ethoxycarbonyl-8-aminooctyl]-L-lysyl-L-proline

N$^\alpha$-[1(S)-ethoxycarbonyl-8-tertiary butoxycarbonylaminooctyl]-N$^\epsilon$-tertiary butoxycarbonyl-L-lysyl-L-proline tertiary butylester obtained by Example VII b) (480 mg) is added into 100 ml of formic acid and dissolved. This solution is stirred at 37° C. for 48 hours. The formic acid is distilled off and the residue is dried under reduced pressure to obtain 320 mg of colorless oil.
TLC, Rf=0.12 (Developing Solvent, B).

(d) N$^\alpha$-[1(S)-carboxy-8-aminooctyl]-L-lysyl-L-proline

The oily substance obtained by Example VII c) (120 mg) is added with 3 ml of aqueous 1N sodium hydrox-

17 ide, and stirred for 2 hours. Then, the mixture is added with acetic acid for acidification. This acidic solution is purified by gel filtration (0.2N acetic acid) using Sephodex LH-20. By freeze-drying the effluence, 58 mg of hydroscopic white powder is obtained.

TLC, Rf=0.02 (Developing Solvent, B).

EXAMPLE VIII $N^\alpha$-[1(S)-carboxy-5-(4-piperidyl)pentyl]-L-lysyl-L-proline (a)

$N^\alpha$-[1(S)-ethoxycarbonyl-5-(1-benzyloxycarbonyl-4-piperidyl)pentyl]-$N^\epsilon$-benzyloxycarbonyl-L-lysyl-L-proline benzylester A solution of ethyl 6-(1-benzyloxycarbonyl-4-piperidyl)-2-oxohexanoate [prepared according to Chem. Pharm. Bull, 34, 3747 (1986)] (7.4 g) and $N^\epsilon$-benzyloxycarbonyl-L-lysyl-L-proline benzylester.trifluoroacetic acid salt (4.6 g) in ethanol (40 ml) is adjusted to pH 5 with triethylamine. To this solution is added 2 g of molecular sieves, and the reaction mixture is stirred for 30 minutes. A solution of sodiumcyanoborohydride (1.4 g) in ethanol (40 ml) is dropped therein under stirring for 5 hours, and is kept stirring for further one night. The ethanol is distilled under reduced pressure, thereafter the residue is transferred to ethyl acetate. The ethyl acetate layer is washed with water, dried with anhydrous sodium sulfate, and concentrated under reduced pressure. To the residue ether is added. The ether layer is washed with water and then ether is distilled under reduced pressure. The residue is applied to silica gel chromatography (ethyl acetate:hexane=2:1) to obtain, from the first effluence, 1.34 g of $N^\alpha$-[1(R)-ethoxycarbonyl-5-(1-benzyloxycarbonyl-4-piperidyl)pentyl]-$N^\epsilon$-benzyloxycarbonyl-L-lysyl-L-proline benzylester (Rf=0.62, expansive solvent, F), and from the following effluence, 1.15 g of $N^\alpha$-[1(S)ethoxycarbonyl-5-(1-benzyloxycarbonyl-4-piperidyl)-pentyl]-$N^\epsilon$-benzyloxycarbonyl-L-proline benzylester (Rf=0.52, expansive solvent, F).

(b)

$N^\alpha$-[1(S)-carboxy-5-(4-piperidyl)pentyl]-L-lysyl-L-proline

The $N^\alpha$-[1(S)-ethoxycarbonyl-5-(1-benzyloxycarbonyl-4-piperidyl)pentyl]-$N^\epsilon$-benzyloxycarbonyl-L-lysyl-L-proline benzylester obtained by Example VIII a) (1.1 g) is dissolved in methanol, and palladium black is added for catalytic reduction. After completion of reaction for 5 hours, the methanol is evaporated in vacuo. The residue is added into 10 ml of 1N-NaOH and dissolved. This solution is left standing at room temperature for 1 hour, and thereafter is treated with cation ion-exchange resin DOWEX 50W-X2. The impurities are removed with 2% pyridine. Then, the eluted fractions by aqueous 4% ammonia are subjected to freeze drying to obtain 300 mg of hygroscopic white powder (Rf=0.08, expansive solvent, B).

18

EXAMPLE XII $N^\alpha$-[1(S)-carboxy-6-(4-piperidyl hexyl]-L-lysyl-L-proline (a)

$N^\alpha$-[1(S)-ethoxycarbonyl-6-(1-benzyloxycarbonyl-4-piperidyl)hexyl]-$N^\epsilon$-benzyloxycarbonyl-L-lysine tertiary butylester A mixture of ethyl 7-(1-benzyloxycarbonyl-4-piperidyl)-2-chloroheptanoate (7.0 g) [prepared according to Chem. Pharm. Bull., 34, 3747 (1986)], $N^\epsilon$-benzyloxycarbonyl-L-lysine tertiary butylester hydrochloride (3.2 g), triethylamine (2.1 g), potassium iodide (5.6 g) and acetonitrile (300 ml) is heated under reflux for 3 days. The mixture is evaporated in vacuo and worked up (AcOEt). The residue is chromatographed on silica gel (hexane:ethyl acetate=2:1) to obtain $N^\alpha$-[1(R)-ethoxycarbonyl-6-(1-benzyloxycarbonyl-4-peperidyl)-hexyl]-$N^\epsilon$-benzyloxycarbonyl-L-lysine tertiary butylester (2.57 g) as a pale yellow oil from the first effluence TLC, Rf=0.31 (Developing Solvent: C, Detection: peptide reagent) and $N^\alpha$-[1(S)-ethoxycarbonyl-6-(1-benzyloxycarbon-4-piperidyl)hexyl]-$N^\epsilon$-benzyloxycarbonyl-L-lysine tertiary butylester (2.66 g) as a pale yellow oil from the second effluence.

TLC, Rf=0.21 (Developing Solvent: C, Detection: peptide reagent).

(b)

$N^\alpha$-[1(S)-ethoxycarbonyl-6-(1-benzyloxycarbonyl-4-piperidyl)hexyl]-$N^\epsilon$-benzyloxycarbonyl-L-lysyl-L-proline tertiary butylester A solution of an oil (2.54 g), obtained by Example XII a), in formic acid (50 ml) is allowed to stand at 40° C. for 40 hours. After evaporation of the solvent, the oil residue is dissolved in water (200 ml). This solution is treated with cation ion-exchange resin DOWEX 50W-X2. Elution with aqueous 2% pyridine and freeze-drying yield a colorless powder (2.0 g).

Then, a solution of diethylphosphorocyanidate (590 mg) in dimethylformamide (DMF 15 ml) is added dropwise to a stirred mixture of the above colorless powder (1.9 g), L-proline tertiary butylester (740 mg) and DMF (40 ml). When the addition is complete, a solution of triethylamine (510 mg) in DMF (5 ml) is added to the mixture. After being stirred for 3 hours, the mixture is diluted with water (300 ml) and extracted with ethyl acetate (900 ml). Ethyl acetate layer is washed with 10% $H_3PO_4$ (150 ml×2), 1N NaOH (60 ml) and water successively, dried ($Na_2SO_4$) and evaporated in vacuo to give an oily residue, which is purified by silica gel column chromatography (hexane:ethyl acetate=1:3) to yield $N^\alpha$-[1(S)-ethoxycarbonyl-6-(1-benzyloxycarbonyl-4-piperidyl)hexyl]-$N^\epsilon$-benzyloxycarbonyl-L-lysyl-L-proline tertiary butylester (2.37 g) as a pale yellow oil.

TLC, Rf=0.54 (Developing Solvent: A, Detection: peptide reagent)

(c)

$N^\alpha$-[1(S)-carboxy-6-(4-piperidyl)hexyl]-L-lysyl-L-proline

A 30% HBr-AcOH solution (10 ml) is added to a solution of an oil, obtained in Example XII b), in AcOH (10 ml). The resulting mixture is allowed to stand for 1 hour and diluted with $Et_2O$ (750 ml). The deposited precipitate is washed with $Et_2O$ and dried to give a crude dihydrobromide salt. Then, a mixture of the above crude salt and 1N NaOH (50 ml) is allowed to stand for 2 hours, and thereafter is treated with cation ion-exchange resin DOWEX 50W-X2. The impurities are removed with aqueous 2% pyridine. Then, the elution with aqueous 4% ammonia and freeze-drying give the desired N$^\alpha$-[1(S)-carboxy-6-(4-piperidyl)hexyl]-L-lysyl-L-proline (700 mg) as a white powder.

TLC, Rf=0.15 (Developing Solvent: B, Detection: ninhydrine)

EXAMPLE XIII

1-[N-[1(S)-carboxy-6-(4-piperidyl)hexyl]-L-alanyl]-(2α,3aβ,7aβ-octahydro-1H-indole-2(S)-carboxylic acid (a)

1-[N-[1(S)-ethoxycarbonyl-6-(1-benzyloxycarbonyl-4-piperidyl)hexyl]-L-alanyl]-(2α,3aβ,7aβ)octahydro-1H-indole-2(S)-carboxylic acid tertiary butylester A solution of N-[1(S)-ethoxycarbonyl-6-(1-benzyloxycarbonyl-4-piperidyl)hexyl]-L-alanine tertiary butylester (850 mg), obtained by Example XIa), in formic acid (18 ml) is allowed to stand at 40° C. for 40 hours. After evaporation of the solvent, the oily residue is dissolved in water (100 ml). This solution is treated with cation ion-exchange resin DOWEX 50W-X2. Elution with aqueous 2% pyridine and freeze-drying yield a colorless powder (640 mg).

Then, a solution of diethylphosphorocyanidate (280 mg) in dimethylformamide (DMF 4 ml) is added dropwise to a stirred mixture of the above colorless powder (640 mg), (2α,3aβ, 7aβ)-octahydro-1H-indole-2(S)-carboxylic acid tertiary butylester (300 mg) [prepared according to J. Med. Chem., 30, 999 (1987)] and DMF (20 ml). When the addition is complete, a solution of triethylamine (250 mg) in DMF (2 ml) is added to the mixture. After being stirred for 3 hours, the mixture is diluted with water (200 ml) and extracted with ethyl acetate (600 ml). The ethyl acetate layer is washed with 10% H$_3$PO$_4$ (100 ml X2), 1N NaOH (60 ml) and water successively, dried (Na$_2$SO$_4$) and evaporated in vacuo to give an oily residue, which is purified by silica gel column chromatoraphy (hexane:ethyl acetate=1:3) to yield 1-[N-[1(S)-ethoxycarbonyl-6-(1-benzyloxycarbonyl-4-piperidyl)hexyl]-L-alanyl)-(2α,3β,7aβ)-octahydro-1H-indole-2(S)-carboxylic acid tertiary butylester (820 mg) as a colorless oil.

TLC, Rf=0.60 (Developing Solvent: A, Detection: peptide reagent).

(b)

1-[N-[1(S)-ethoxycarbonyl-6-(4-piperidyl)hexyl]-L-alanyl]-(2α,3aβ,7aβ)-octahydro-1H-indole-2(S)-carboxylic acid dihydrobromide A 25% HBr-AcOH solution (4 ml) is added to a solution of an oil, obtained by Example XIII a), in AcOH (4 ml). The resulting mixture is allowed to stand for 1 hour and diluted with Et$_2$O (300 ml). The deposited precipitate is washed with Et$_2$O and dried to give the desired 1-[N-[1(S)-ethoxycarbonyl-6-(4-piperidyl)hexyl]-L-alanyl]-(2α,3aβ,7aβ)-octahydro-1H-indole-2(S)-carboxylic acid dihydrobromide (530 mg) as a colorless powder.

TLC, Rf=0.53 (Developing Solvent: B, Detection: ninhydrine).

(c)

1-[N-[1(S)-carboxy-6-piperidyl)hexyl]-L-alanyl]-(2α,3aβ,7aβ)-octahydro-1H-indole-2(S)-carboxylic acid A mixture of a monoacid (400 mg), obtained by Example XIII(b), and 1N NaOH (50 ml) is allowed to stand for 2 hours, and thereafter is treated with cation ion-exchange resin DOWEX 50W-X2. Elution with 2% aqueous pyridine and freeze-drying give the desired 1-[N-[1(S)-carboxyl-6-(4-piperidyl)hexyl]-L-alanyl]-(2α,3aβ,7aβ)-octahydro-1H-indole-2(S)-carboxylic acid (250 mg) as a white powder.

TLC, Rf=0.33 (Developing Solvent: B, Detection: ninhydrine).

EXAMPLE XIV

1-[N-[1(S)-carboxy-5-(4-piperidyl)pentyl]-L-alanyl]-(2α,3aβ,7aβ)-octahydro-1H-indole-2(S)-carboxylic acid (a)

1-[N-1(S)-ethoxycarbonyl-5-(1-benzyloxycarbonyl-4-piperidyl)pentyl]-L-alanyl]-(2α,3aβ,7aβ)-octahydro-1H-indole-2(S)-carboxylic acid tertiary butylester According to the method for the preparation of Example XIII (a), N-[1(S)-ethoxycarbonyl-5-(1-benzyloxycarbonyl-4-piperidyl)pentyl]-L-alanine (300 mg), obtained by Example X(a), is coupled with (2α,3aβ,7aβ)-octahydro-1H-indole-2(S)-carboxylic acid tertiary butylester (165 mg) (prepared according to J. Med. Chem., 30, 999 (1987)] in the presence of diethylphosphorocyanidate to yield 1-[N-[1(S)-ethoxycarbonyl-5-(1-benxyloxycarbonyl-4-piperidyl)pentyl]-L-alanyl]-(2α,3aβ,7aβ)-octahydro-1H-indole-2(S)-carboxylic acid tertiary butylester (310 mg) as a colorless oil.

TLC, Rf=0.50 (Developing Solvent: A, Detection: peptide reagent).

(b)

1-[N-[1(S)-ethoxycarbonyl-5-(4-piperidyl)pentyl]-L-alanyl]-(2α,3aβ,7aβ)-octahydro-1H-indole-2(S)-carboxylic acid dihydrobromide According to the method for the preparation of Example XIII b), deprotection of an oil (Example XIV a), 310 mg) and purification of the product are carried out to yield 1-[N-[1(S)-ethoxycarbonyl-5-(4-piperidyl)pentyl]-L-alanyl)-(2α,3aβ,7aβ)-octahydro-1H-indole-2(S)-carboxylic acid dihydrobromide (245 mg) as a colorless powder.

TLC, Rf=0.26 (Developing Solvent: B, Detection: ninhydrine).

(c)

1-[N-[1(S)-carboxy-5-(4-piperidyl)pentyl]-L-alanyl]-(2α,3aβ,7aβ)-octahydro-1H-indole-2(S)-carboxylic acid According to the method for the preparation of Example XIII c), saponification of a monoacid (Example XIV b), 210 mg) and purification of the product are carried out to yield 1-[N-[1(S)-carboxy-5-(4-piperidyl)pentyl]-L-alanyl]-(2α,3aβ,7aβ)-octahydro-1H-indole-2(S)-carboxylic acid (114 mg) as a white powder.

TLC, Rf=0.19 (Developing Solvent: B, Detection: ninhydrine).

What is claimed is:
1. A compound of the formula:

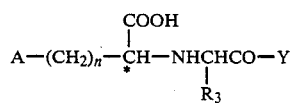

wherein

A is —NH₂ or

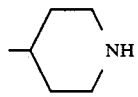

Y is

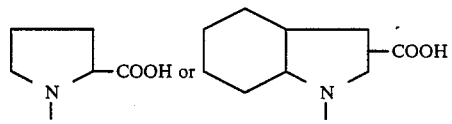

R₃ is —CH₃ or —(CH₂)₄NH₂ n represents a number of from 3 to 8, with the proviso than when A is amino, n is 7 or 8, and a pharmaceutical acceptable salt thereof.

2. An alanine derivative of the formula:

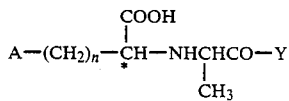

wherein

A is —NH₂ or

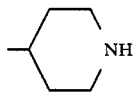

Y is

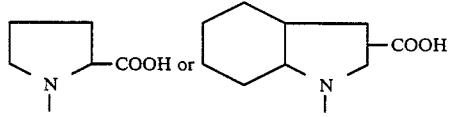

n represents a number of from 3 to 8, with the proviso than when A is amino, n is 7 or 8, and a pharmaceutical acceptable salt thereof.

3. A lysine derivative of the formula:

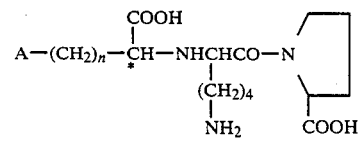

wherein

A is —NH₂ or

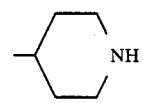

n represents a number of from 3 to 8, with the proviso than when A is amino, n is 7 or 8, and a pharmaceutical acceptable salt thereof.

4. Compounds of claim 1, 2 or 3 in which the star marked carbon is of the S-configuration and the other absolute configurations are those of L-amino acids.

5. A compound of claim 2 which is N-[1-(s)-carboxy-8-aminooctyl]-L-alanyl-L-proline.

6. A compound of claim 2 which is N-[1-(s)-carboxy-9-aminononyl]-L-alanyl-L-proline.

7. A compound of claim 2 which is N-[1-(s)-carboxy-3-(4-piperidyl)propyl]-L-alanyl-L-proline.

8. A compound of claim 2 which is N-[1-(s)-carboxy-5-(4-piperidyl)pentyl]-L-alanyl-L-proline.

9. A compound of claim 2 which is N-[1-(s)-carboxy-6-(4-piperidyl)hexyl]-L-alanyl-L-proline.

10. A compound of claim 2 which is 1-[N-[1(s)-carboxy-6-(4-piperidyl)hexyl]-L-alanyl]-2α,3aβ,7aβ)-octahydro-1H-indole-2(s)-carboxylic acid.

11. A compound of claim 2 which is 1-[N-[1(s)-carboxy-5-(4-piperidyl)pentyl]-L-alanyl]-2α,3aβ,7aβ)-octahydro-1H-indole-2(s)-carboxylic acid.

12. A compound of claim 3 which is Nα-[1(s)-carboxy-8-aminooctyl]-L-lysyl-L-proline.

13. A compound of claim 3 which is Nα-[1(s)-carboxy-5-(4-piperidyl)pentyl]-L-lysyl-L-proline.

14. A compound of claim 3 which is Nα-[1(s)-carboxy-6-(4-piperidyl)hexyl]-L-lysyl-L-proline.

* * * * *

UNITED STATES PATENT AND TRADEMARK OFFICE
CERTIFICATE OF CORRECTION

PATENT NO. : 4,897,483

DATED : January 30, 1990

INVENTOR(S) : Shizuo Saito, et al.

It is certified that error appears in the above-identified patent and that said Letters Patent is hereby corrected as shown below:

Col. 3, line 8: after "propyl]-" delete "1" and insert -- L --.

Col. 3, line 22: delete "$(2_{60}$" and insert -- $(2_{\alpha}$ --.

Col. 3, line 24: delete "1-[N-" and insert -- 2-[N- --.

Col. 6, line 26: delete "instrance" and insert -- instance --.

Signed and Sealed this

Sixth Day of August, 1991

Attest:

HARRY F. MANBECK, JR.

Attesting Officer

Commissioner of Patents and Trademarks